US012698519B2

(12) United States Patent　　(10) Patent No.:　US 12,698,519 B2

Matsubara et al.　　(45) Date of Patent:　Aug. 4, 2026

(54) CHEMICAL SUSCEPTIBILITY INSPECTION METHOD

(71) Applicants: Hitachi High-Tech Corporation, Tokyo (JP); IHU Mediterranee Infection, Marseilles Cédex (FR)

(72) Inventors: Shigeki Matsubara, Tokyo (JP); Yuusuke Oominami, Tokyo (JP); Kyoko Imai, Tokyo (JP); Takashi Irie, Tokyo (JP); Didier Raoult, Marseilles Cédex (FR); Jacques Bou Khalil, Marseilles Cédex (FR)

(73) Assignees: Hitachi High-Tech Corporation, Tokyo (JP); IHU Mediterranee Infection, Marseilles Cedex (FR)

( * ) Notice: Subject to any disclaimer, the term of this patent is extended or adjusted under 35 U.S.C. 154(b) by 220 days.

(21) Appl. No.: 17/255,312

(22) PCT Filed: Mar. 14, 2019

(86) PCT No.: PCT/FR2019/050576
§ 371 (c)(1),
(2) Date: Dec. 22, 2020

(87) PCT Pub. No.: WO2020/183072
PCT Pub. Date: Sep. 17, 2020

(65) Prior Publication Data
US 2021/0269847 A1　　Sep. 2, 2021

(51) Int. Cl.
*C12Q 1/18*　　(2006.01)
*C12Q 1/04*　　(2006.01)

(52) U.S. Cl.
CPC ............... *C12Q 1/18* (2013.01); *C12Q 1/04* (2013.01)

(58) Field of Classification Search
CPC .......... C12Q 1/18; C12M 33/00; C12M 41/30
See application file for complete search history.

(56) References Cited

U.S. PATENT DOCUMENTS

2001/0039032 A1　11/2001　Matsumura et al.
2005/0130253 A1　6/2005　Lye et al.
(Continued)

FOREIGN PATENT DOCUMENTS

EP　　2 757 371 A1　7/2014
EP　　3 121 262 A1　1/2017
(Continued)

OTHER PUBLICATIONS

Japanese-language Office Action issued in Japanese Application No. 2021-517917 dated Jul. 26, 2022 with English translation (six (6) pages).
(Continued)

*Primary Examiner* — Jana A Hines
(74) *Attorney, Agent, or Firm* — Crowell & Moring LLP

(57) ABSTRACT

The purpose of this invention is to provide an inspection method which enables us to judge a microbe's chemical susceptibility quickly, versatile and cheap. The inspection method of this invention's one aspect comprises a step for judging the chemical susceptibility to the antimicrobial of the microbe based on appearance-changing of the observed microbe. The step for judging may judge the chemical susceptibility by obtaining a feature of the plurality of images in the database regarding a plurality of images of microbes which have already been confirmed that they are resistant microbes and a plurality of images of microbes which have already been confirmed that they have susceptibility to an antimicrobial by machine learning and by comparing the images of the microbes with the images in the database based on the feature. Furthermore, the step for judging may judge the chemical susceptibility based on an abundance ratio of the microbe whose appearance changed out of the microbe in the field.

7 Claims, 6 Drawing Sheets

(56) References Cited

U.S. PATENT DOCUMENTS

| | | |
|---|---|---|
| 2006/0134728 A1 | 6/2006 | MacDonald et al. |
| 2007/0231887 A1 | 10/2007 | McGrath et al. |
| 2012/0190632 A1 | 7/2012 | Chen et al. |
| 2013/0017534 A1 | 1/2013 | Nickel et al. |
| 2014/0162308 A1 | 6/2014 | Nickel et al. |
| 2014/0278136 A1 | 9/2014 | Shamsheyeva et al. |
| 2014/0349333 A1 | 11/2014 | Matsumoto et al. |
| 2016/0289729 A1* | 10/2016 | Richards ................ G01N 1/38 |
| 2017/0096631 A1 | 4/2017 | Uematsu et al. |
| 2017/0121759 A1 | 5/2017 | Jarvius et al. |
| 2018/0010084 A1 | 1/2018 | Uematsu et al. |
| 2018/0079996 A1 | 3/2018 | Minekawa et al. |
| 2018/0342078 A1 | 11/2018 | Watanabe |
| 2020/0399581 A1 | 12/2020 | Uematsu et al. |

FOREIGN PATENT DOCUMENTS

| | | | |
|---|---|---|---|
| EP | 3252138 A1 * | 12/2017 | .............. C12M 1/34 |
| EP | 3 287 515 A1 | 2/2018 | |
| JP | 10-14595 A | 1/1998 | |
| JP | 2001-275696 A | 10/2001 | |
| JP | 2002-205902 A | 7/2002 | |
| JP | 2003-505106 A | 2/2003 | |
| JP | 2005-261260 A | 9/2005 | |
| JP | 2007-514952 A | 6/2007 | |
| JP | 2009-36694 A | 2/2009 | |
| JP | 2009-529888 A | 8/2009 | |
| JP | 2010-213598 A | 9/2010 | |
| JP | 2012-153687 A | 8/2012 | |
| JP | 2016-136876 A | 8/2014 | |
| JP | 2015-177768 A | 10/2015 | |
| JP | 2017-518768 A | 7/2017 | |
| WO | WO 01/09371 A1 | 2/2001 | |
| WO | WO 2012/151563 A2 | 11/2012 | |
| WO | WO 2013/038925 A1 | 3/2013 | |
| WO | WO 2014/145899 A1 | 9/2014 | |
| WO | WO 2015/189390 A1 | 12/2015 | |
| WO | WO 2017/061155 A1 | 4/2017 | |
| WO | WO 2018/096153 A1 | 5/2018 | |
| WO | WO 2018/136864 A1 | 7/2018 | |
| WO | WO 2018/174784 A1 | 9/2018 | |

OTHER PUBLICATIONS

International Search Report (PCT/ISA/210) issued in PCT Application No. PCT/FR2019/050576 dated Dec. 6, 2019 with English translation (eight (8) pages).

French-language Written Opinion (PCT/ISA/237) issued in PCT Application No. PCT/FR2019/050576 dated Dec. 6, 2019 (nine (9) pages).

Japanese-language Office Action issued in Japanese Application No. 2021-517917 dated Jan. 25, 2022 (five (5) pages).

Chinese-language Office Action issued in Chinese Application No. 201980042629.3 dated May 6, 2023, with English translation (17 pages).

Yue X. et al., "Morphological Changes of Dermatophy Test Treated by Terbinafine", Chin J Derm Venereo, Aug. 2008, pp. 464-466, vol. 22, No. 8, with English Abstract (3 pages).

Yun L. et al., "The antibiotic resistance analysis and the physiological change of Acinetobacter baumanii", Int J Lab Med, Oct. 2013, pp. 2650-2651, 2655, vol. 34, No. 20 with English abstract (3 pages).

Chinese-language Office Action issued in Chinese Application No. 201980042629.3 dated Mar. 26, 2023 with English translation (18 pages).

Kim, P., "Deep Learning for Beginners: with MATLAB Examples", Jin Shengjian, Beijing University of Aeronautics and Astronautics, Apr. 30, 2018, p. 7 (4 Pages).

* cited by examiner

[FIG. 1]
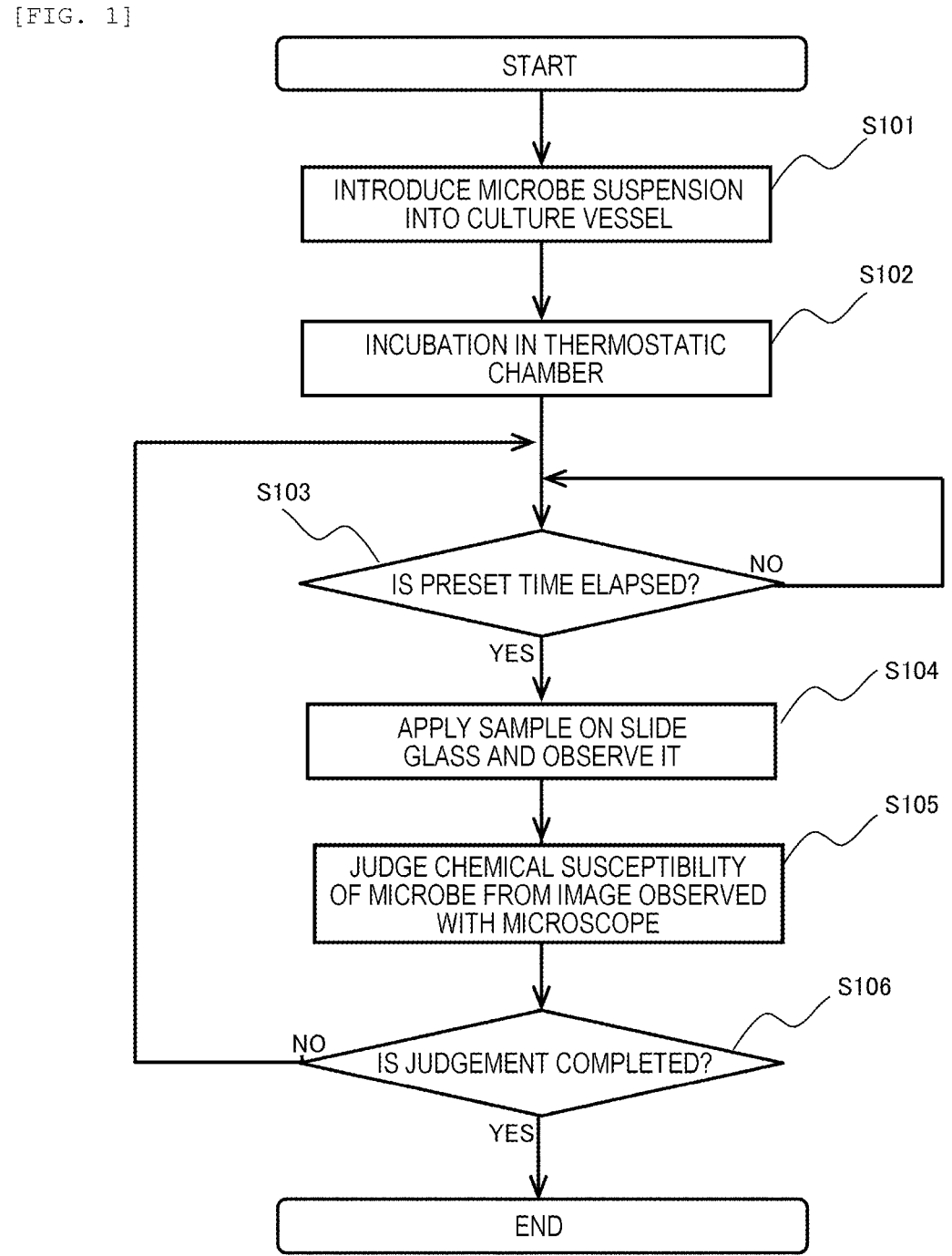

[FIG. 2]
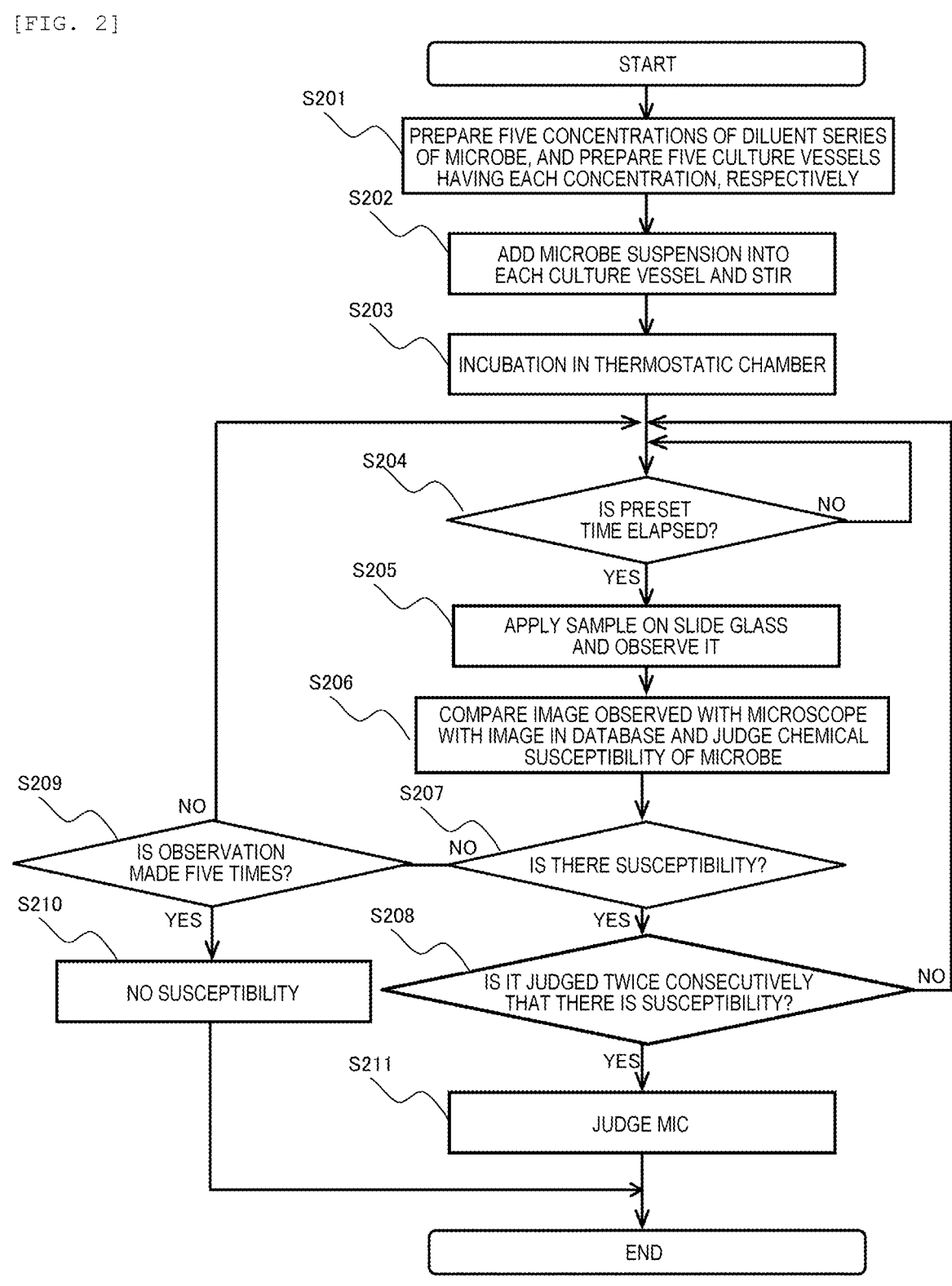

[FIG. 3]
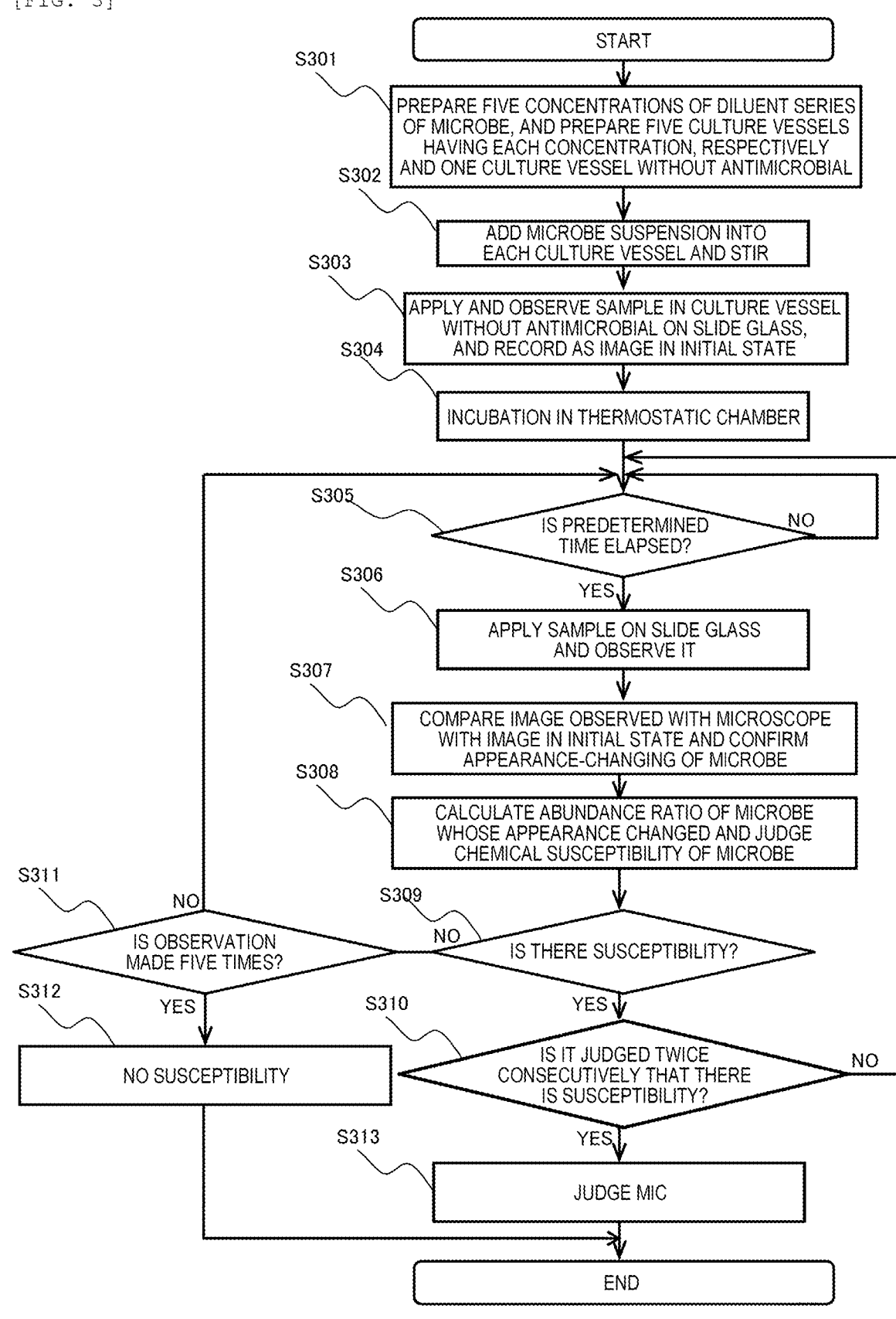

[FIG. 4]

| MICROBE SPECIES | ANTIMICROBIAL |
| --- | --- |
| Staphyloccocus aureus | Methicillin |
| Staphyloccocus aureus | Vancomycin |
| Staphyloccocus aureus | Gentamicin |
| Klebsiella pneumoniae | Imipenem |
| Klebsiella pneumoniae | Colistin |
| Acinetobacter baumannii | Imipenem |
| Acinetobacter baumannii | Colistin |
| Escherichia coli | Imipenem |
| Pseudomonas aeruginosa | Imipenem |
| Pseudomonas aeruginosa | Colistin |
| Proteus vulgaris | Imipenem |
| Enteroccocus faecalis | Gentamicin |
| Enteroccocus faecalis | Vancomycin |
| Enterobacter cloacae | Imipenem |
| Stenotrophomonas maltophilia | Imipenem |

FIG. 5A                    FIG. 5B
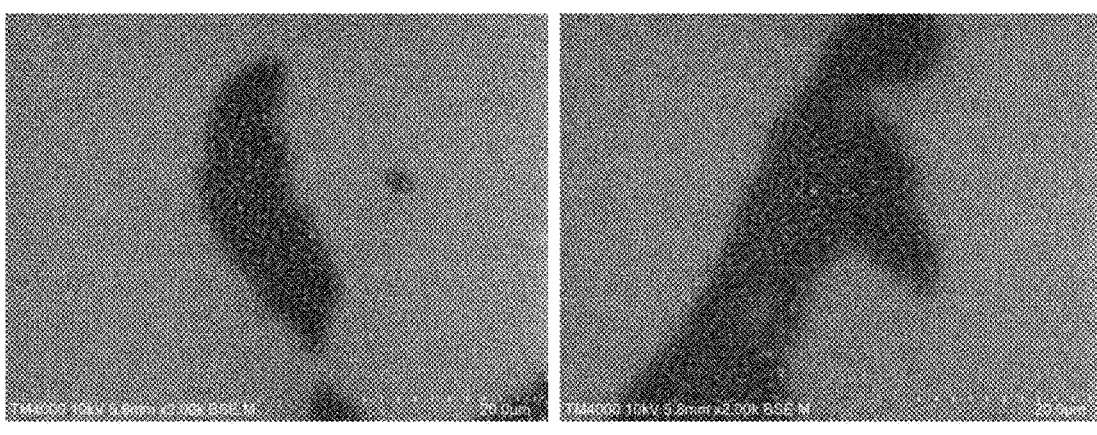
FIG. 5C                    FIG. 5D
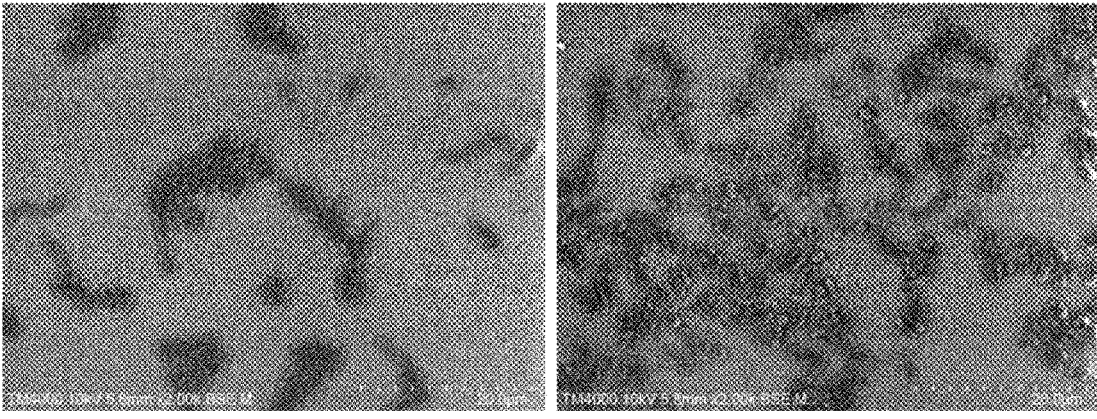

CHEMICAL SUSCEPTIBILITY INSPECTION METHOD

TECHNICAL FIELD

The present invention relates to a chemical susceptibility inspection method.

BACKGROUND ART

An inspection apparatus for acquiring images of microbe colonies in a culture dish and measuring microbe and cells, and the like have been developed in an effort to promote automation and labor saving of the culture separation for use in test laboratories (PTL 1). In addition, in order to shorten the time required for the inspection, an inspection apparatus has been disclosed, which has a plurality of wells in a culture plate that holds a culture fluid containing microbe or fungi in each well and microscopically observes microbe or fungi in the culture fluid contained in each well (PTL 2).

CITATION LIST

Patent Literature

PTL 1: JP-A-2005-261260.3
PTL 2: JP-A-2015-177768

SUMMARY OF INVENTION

Technical Problem

However, in the apparatus according to Patent Document 1, since it is necessary that the microbe grow enough to be judged, in the case of slow growing microbe such as *Pseudomonas aeruginosa*, it takes eight hours or longer for culturing until a single colony is obtained.

In addition, in the apparatus according to Patent Document 2, while the inspection time is shortened by utilizing microscopic observation of microbe that judges the shape of each microbe, since a dedicated device having a complicated mechanism and a dedicated culture plate are required, it is inevitable that the inspection cost is increased.

Accordingly, an object of the present invention is to provide an inspection method which enables us to judge a microbe's chemical susceptibility quickly, versatile and cheap.

Solution to Problem

The inspection method of an aspect of the invention includes a step for judging the chemical susceptibility to the antimicrobial of the microbe based on appearance-changing of the observed microbe. The step for judging may judge the chemical susceptibility by obtaining a feature of the plurality of images in the database regarding a plurality of images of microbes which have already been confirmed that they are resistant microbes and a plurality of images of microbes which have already been confirmed that they have susceptibility to an antimicrobial by machine learning and by comparing the images of the microbes with the images in the database based on the feature. Furthermore, the step for judging may judge the chemical susceptibility based on an abundance ratio of the microbe whose appearance changed out of the microbe in the field.

Advantageous Effects of Invention

According to the present invention, it is possible to provide an inspection method that accelerates a judgment of a chemical susceptibility of a microbe.

BRIEF DESCRIPTION OF DRAWINGS

FIG. 1 is a diagram illustrating a judgment flow of an inspection method of a chemical susceptibility of a microbe.
FIG. 2 is a diagram illustrating a detailed judgment flow of an inspection method according to a first embodiment.
FIG. 3 is a diagram illustrating a detailed judgment flow of an inspection method according to a second embodiment.
FIG. 4 is a diagram illustrating microbes and antibiotics as main subjects.
FIGS. 5A to 5D are views illustrating Example 1 of electron microscope images.

DESCRIPTION OF EMBODIMENTS

Figures 6A, 6B:
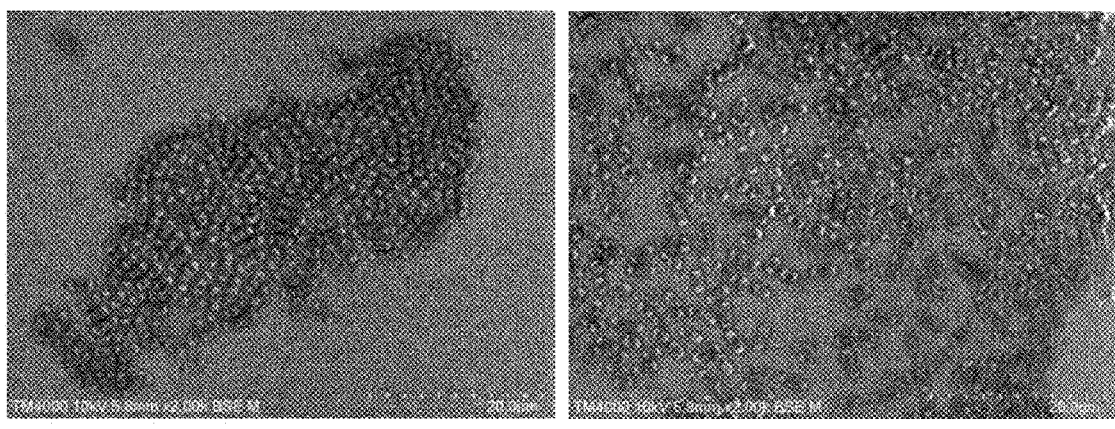
FIGS. 6A to 6D are views illustrating Example 2 of electron microscope images.

Hereinafter, examples will be described with reference to the accompanying drawings. FIG. 1 is a diagram illustrating a judgment flow of an inspection method of a chemical susceptibility of a microbe.

As used herein, a microbial chemical susceptibility test refers to inspecting whether the same strains are drug-resistant or not based on the conditions under which the microbes are proliferated in a culture of microbes cultured in a culture medium containing various antimicrobials at a predetermined concentration, or judging minimum inhibitory concentration (MIC) of microbe. Here, 'microbe' includes 'bacteria' and 'fungi'. Furthermore, the bacteria as a subject of inspection by this method is not particularly limited. For example, the bacteria includes *Staphylococcus aureus*, enterococci, pneumococcus, *Escherichia coli, Pseudomonas aeruginosa, Klebsiella pneumoniae* and the like.

When conducting a test according to this method, microbe suspension is often prepared using single colony obtained from clinical sample by separate culture. Meanwhile, when the clinical sample has low possibility of contamination and contains a single microbe, the sample may be used as it is or diluted appropriately without preparing a microbe suspension. In addition, it is desirable to follow the method recommended by Clinical and Laboratory Standards Institute (CLSI) for harvest and transport of samples, separation culture, preparation of antimicrobial, preparation of medium, culture temperature, culture fluid, and the like, but not limited thereto.

Next, the culturing procedure will be described. First, a microbe suspension prepared from a sample is introduced into a culture vessel (hereinbelow, referred to as 'vessel') (S101). Then, the microbe suspension mixed with the culture fluid each containing different antimicrobials at a specific concentration in each vessel is incubated and cultured in a thermostatic chamber set at about 35° C. (S102). At this time, a sample mixed with the culture fluid without antimicrobial is cultured as a control sample at the same time. Then it is determined whether a predetermined preset time has elapsed (S103). When the predetermined time has elapsed, the vessel is taken out from the thermostatic chamber, and a sample in the vessel the culture fluid mixed with the microbe suspension is applied onto a slide glass and observed with a microscope. At this time, pretreatment such as staining or the like is not necessarily required. Then, the chemical susceptibility (hereinafter, referred to as "sensitivity") of the microbe is judged from the microscopic image (S104). Thereafter, it is determined whether or not the judging is to be ended (S106), and if it is determined that the determination is to be ended, the process is ended.

The observation may be performed at preset time intervals from the start to the end of incubation, and the appearance of microbe proliferation may be continuously monitored. In addition, an appropriate time may be set, in which case monitoring may be performed at the set time and compared with a monitoring result obtained at the start of the incubation. In addition, a plurality of culture vessels containing a microbe suspension and a specific concentration of antimicrobial may be prepared in advance, and the microbe suspension in different vessels may be observed each time a predetermined time elapses. In addition, the antimicrobial's concentration may not be specified, and a ratio of microbe suspension and an antimicrobial may be specified.

Example 1

FIG. 2 is a diagram showing a detailed judgment flow of an inspection method according to the first embodiment. In Example 1, a plurality of images of microbe that have been confirmed to be resistant microbe and a plurality of images of microbe that have been confirmed to have susceptibility to an antimicrobial are put into a database.

First, five concentrations of dilution series of antimicrobial are prepared, and five vessels containing each concentration are prepared (S201). This is to make it possible to observe each of the series five times at predetermined time intervals (for example, every 30 minutes). However, the time intervals of observation and the number of observations are not limited to the above. Next, the microbe suspension is introduced into each culture vessel and stirred (S202), and 25 vessels are placed in a thermostatic chamber set at 35° C. and incubated in the thermostatic chamber (S203). Next, it is determined whether a predetermined preset time has elapsed (S204). When the predetermined time has elapsed, each of the 5 concentration vessels is taken out one by one, and the sample in the taken out vessel is applied onto a slide glass and observed (S205). It is then judged whether the microbe is a resistant microbe or has susceptibility by comparing the microscopic images with the images in the database (S206).

Here, it is judged whether the microbe has susceptibility (S207), and if judging that the microbe has susceptibility, it is judged again (twice consecutively) whether the microbe has susceptibility (S208). When it is judged both of the two times that the sample containing the specific antimicrobial agent concentration has susceptibility, the lowest antimicrobial agent concentration among the samples that are judged to have susceptibility is judged to be MIC (S211), and the process is ended.

In S207, when it is judged that the microbe does not have susceptibility, it is judged whether observation has been made for five times (S209). When judging that the observation has been made for five times, it is judged that there is no susceptibility (S210) and the process is ended, and if judging that the observation has not been made for five times, the process returns to S204.

Further, when determining that there is no susceptibility in S207 or S208, or after the predetermined time has elapsed, similarly, an image observed with an electron microscope is acquired and compared with the image of the database to judge whether the microbe is the resistant microbe or has the susceptibility. Thereafter, observed images are acquired every when the predetermined time has elapsed. When it is determined that sample has susceptibility to all antimicrobial concentrations, or when the observation of the samples in all the vessels are completed, the lowest antimicrobial concentration among the samples judged to have susceptibility is judged to be MIC.

Software capable of automatic discrimination may be used to compare the images in the database with the images acquired with the electron microscope. The software may automatically generate discrimination algorithms by mechanically learning the features of images in the database. In addition, at appropriate timing, the images of the microbe that have been confirmed to be resistant microbe and/or the images of microbe confirmed to have susceptibility to an antimicrobial may be additionally registered to the database. Furthermore, the software may update discrimination algorithms by mechanically learning the features of images concluding additionally registered images in the database, continuously.

Example 2

FIG. 3 is a diagram showing a detailed judgment flow of an inspection method according to a second embodiment.

First, five concentrations of dilution series of antimicrobial are prepared, and five vessels containing each concentration are prepared (S301). The interval time of observation and the number of observations are the same as in Example 1. Next, the microbe suspension is introduced into each vessel and stirred (S302), and a sample in the vessel not containing an antimicrobial is applied onto a slide glass and observed with the electron microscope to obtain an image in an initial state (S303).

Next, 25 vessels are placed in a thermostatic chamber set at 35° C. and incubated in the thermostatic chamber (S304). After a predetermined time (S305), each of the five concentration vessels is taken out one by one, and the sample in the vessel is applied onto a slide glass and observed with the electron microscope (S306). Further, appearance information of whole microbe, which is constructed by gathering appearance data of the observed microbe, and a total number of the microbe in the plurality of fields is recorded, and an image acquired by the electron microscopic observation is compared with the image in the initial state to confirm whether there is a microbe whose appearance changed (S307).

Here, the appearance of the microbe indicates a shape of the microbe and/or a brightness of the region where the microbe exists. For example, the shape may include roundness, ratio of longer axis/shorter axis, area of occupancy, area of clusters formed by a plurality of microbes, the number of microbes within the cluster, microbial density within the cluster, and the like, and brightness may include, for example, contrast ratio and the like. In addition, the shape may be a shape of a cluster when a plurality of the microbes form the cluster, and/or a shape of each microbe which is independent of the cluster.

The situation that the regions whose brightness are high (hyper-dense spots) appear during cell division of microbes is confirmed. For example, when the cell division of *Bacillus* begins, the brightness of the *Bacillus*'s periphery, especially, longer direction's both extremities gets higher. If the division proceeds more and more, the brightness of division parts generated the vicinity of the center of original cell also gets higher. In this way, if we observe the change of the brightness, then we can confirm that the appearance of microbes changed.

When there are microbes whose appearance changed, the number of the microbes whose appearance changed existing in the field is recorded, and an abundance ratio of the microbes whose appearance changed is calculated from the total number of microbes and the number of microbes whose appearance changed.

When the calculated abundance ratio exceeds a predetermined value set in advance, it is judged that the microbe has susceptibility to an antimicrobial. In addition, when 60 minutes have elapsed, an image observed with the electron microscope is acquired, and the abundance ratio of the number of microbes whose appearance changed is calculated to judge whether the microbe is the resistant microbe or has the susceptibility (S308). The subsequent processes are same as in Example 1.

One sample may be observed, in which case images in respective fields are acquired, the total number of microbes and the number of microbes whose appearance changed in each field are recorded, the number of microbes in all fields is totaled, and the abundance ratio of microbes whose appearance changed may be calculated. It is desirable that the total number of all microbes be equal to or greater than 1,000, although not limited to that figure.

In judging whether or not a microbe is resistant microbe, when the time-changing of the calculated abundance ratio (for example, the time-changing from the initial state of the abundance ratio) exceeds a certain value set in advance, it may be determined that the microbe has susceptibility to an antimicrobial. In addition, a combination of judgment methods may be used. For example, judgement may be made based on the abundance ratio after 30 minutes elapsed and then made based on by the rate of change of the abundance ratio after 60 minutes elapsed.

In addition, an appearance information in case that the antimicrobial is given to a microbe a predetermined person has, may be compared with an appearance information in case that the antimicrobial is not given to a microbe the predetermined person has, and the susceptibility to the antimicrobial of the microbe the predetermined person has may be judged based on the result from the comparison.

In addition, a criterion may be obtained regarding abundance ratio of appearance-changing, made based on antimicrobial of a predetermined standard microbe and a predetermined concentration, and susceptibility of a microbe a predetermined person has may be judged based on the criterion.

For discrimination of microbe whose appearance changed in the image, software capable of automatic discrimination may be used. The software may automatically generate discrimination algorithms by mechanically learning the features of appearance changes from a database of images of microbe in an initial state prepared in advance and from a database of images of microbe whose appearance changed due to the influence of an antimicrobial. In addition, software for automatically judging and recording the number of microbes may be used.

FIG. 4 is a diagram illustrating microbes and antibiotics as main subjects. The appearance features that appear later show indications that enable to detect susceptibility or resistance to antimicrobial. Below are some examples as confirmed so far.

In gram-negative microbe, strong refraction or angle of refraction of electron beam is observed at both ends of cell division during growth phase. When microbes have susceptibility to an antimicrobial for inspection, there are few microbes with a refractive appearance of the electron beam, and the ratio between microbes without refraction and microbes with refraction is noticeable in the initial state. At a later stage, the susceptible microbes show elongation of the cells, three branches, two branches, micronization and spheronization.

In gram-positive cocci such as *Staphylococci*, it has been observed that the susceptible microbe has enlarged body.

FIG. 5 is a view showing Example 1 of an electron microscope image showing a result of culturing *Escherichia coli* in a culture fluid containing 1 mg/L of imipenem. In FIG. 5, (a) and (b) show images of microbes confirmed to be resistant to imipenem, (c) and (d) show images of microbes confirmed to have susceptibility to imipenem, and (a) to (d) show the states after 30 minutes, 120 minutes, 30 minutes, and 120 minutes from the start of culture, respectively. The resistant microbes in both (a) and (b) form clusters, but the cluster in (c) is very small, and in (d), no cluster is formed. In addition, a brightness of the microbes in (c) and (d) is higher than that in (a) and (b). Although it is possible to confirm the outline of the microbe without staining by using the optical microscope, it is difficult to obtain more detailed appearance information for individual microbe.

Figures 6C, 6D:
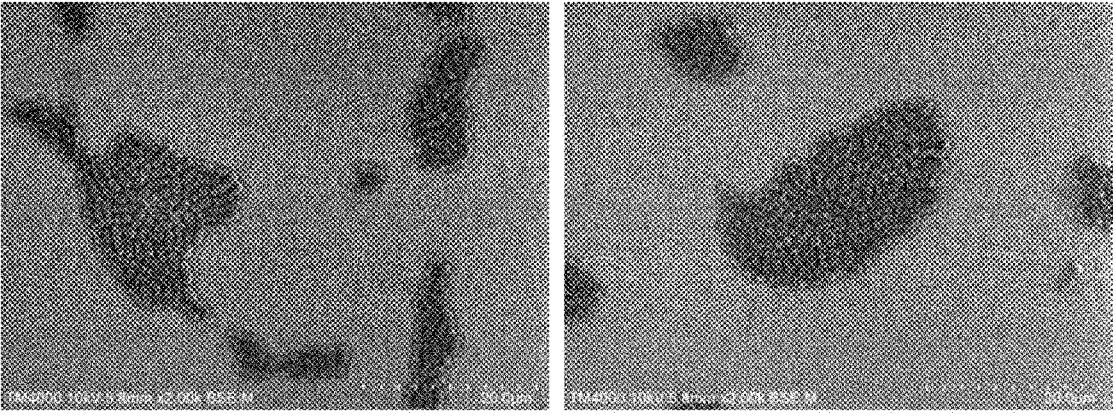

FIG. 6 is a view showing Example 2 of an electron microscope image showing a result of culturing *Klebsiella pneumonia* in a culture fluid containing 1 mg/L of imipenem. In FIG. 6, (a) and (b) show images of microbes confirmed to be resistant to imipenem, (c) and (d) show images of microbes confirmed to have susceptibility to imipenem, and (a) to (d) show the states after 30 minutes, (120 minutes, 30 minutes, and 120 minutes from the start of culture, respectively. It can be confirmed that in (a) and (b), the density of the cluster formed by the microbes is low, whereas in (c) and (d), the cluster is formed in a high density state. In addition, it can be confirmed that, while (a) and (b) show division growth in many microbes, in (c) and (d), there is no division, and each microbe has a shape of appearance with a long axis shortened to a shape close to a circle. It can also be confirmed that a brightness of the microbes in (c) and (d) is lower than that in (a) and (b).

In the present embodiment, it is described that observation is performed using an electron microscope, but, for example, the electron microscope may refer to a scanning electron microscope (SEM), a desk scanning electron microscope or a scanning electron microscope which is observable in an atmospheric pressure or a scanning probe microscope.

The invention claimed is:

1. An inspection method for inspecting susceptibility of a first microbe to an antimicrobial, comprising:

mixing the first microbe in a culture fluid with the antimicrobial at a predetermined concentration to prepare the antimicrobial sample;

keeping the antimicrobial sample and a control sample warm at a temperature above room temperature, the control sample comprising a culture fluid comprising a second microbe that is of a same strain as the first microbe, the control sample without the antimicrobial;

observing the antimicrobial sample comprising the first microbe at an initial time and at a plurality of time intervals by a microscope, and observing the control sample comprising the second microbe at at least one of the plurality of time intervals by the microscope, the initial time being a time zero at which the first microbe is not influenced by the antimicrobial;

counting a number of the first microbe in a field of the microscope at one of the plurality of time intervals after mixing the culture fluid containing the first microbe with the antimicrobial;

analyzing an appearance of an observed first microbe and comparing a first image regarding an appearance of the observed first microbe with a second image regarding an appearance of an observed second microbe at at least one of the plurality of time intervals;

discriminating microbes with a change in appearance since the initial time from the first microbe;

calculating an abundance ratio of a number of the microbes with a change in appearance compared to the number of the first microbe in the field, when the abundance ratio exceeds a predetermined value, the microbe is judged to have susceptibility to the antimicrobial, and the judging is confirmed twice consecutively; and determining a minimum inhibitory concentration of the antimicrobial to the first microbe based on an appearance-changing of the observed first microbe, from the initial time to one of the plurality of time intervals, wherein the minimum inhibitory concentration is the lowest antimicrobial concentration among two antimicrobial samples that are judged to have susceptibility to the antimicrobial;

wherein the microscope is a scanning electron microscope or a scanning probe microscope;

wherein samples observed by the microscope consists of the antimicrobial sample and the control sample.

2. The inspection method according to claim 1, further comprising:

putting a plurality of images of drug-resistant microbes into a database;

putting a second plurality of images of microbes that are not drug-resistant into the database; and obtaining a feature of the plurality of images and the second plurality of images in the database by machine learning, the feature comprising a ratio between microbes without refraction and microbes with refraction at the initial time, cell elongation, micronization, and spheronization; and wherein the determining comprises comparing the first image and the second image with the plurality of images and the second plurality of images in the database based on the feature.

3. The inspection method according to claim 1, wherein the appearance of the observed first microbe or the observed second microbe is a shape of the observed first microbe or the observed second microbe, and/or a brightness of the region where the observed first microbe or the observed second microbe exists.

4. The inspection method according to claim 3, wherein the shape of the observed first microbe or the observed second microbe is a shape of a group in case that a plurality of the observed first microbes or a plurality of the observed second microbes form a group, and/or a shape of each observed first microbe or each observed second microbe that is independent of the group.

5. The inspection method according to claim 1, wherein the observing comprises observing a same antimicrobial sample in a plurality of fields by the microscope, and the calculating comprises determining the abundance ratio of the number of the microbes whose appearance changed based on a total number of the microbes in the plurality of fields.

6. The inspection method according to claim 1, wherein the determining is based on time-changing of the abundance ratio.

7. The inspection method according to claim 1, wherein the analyzing comprises obtaining an appearance information of a whole microbe constructed by gathering appearance data of an observed microbe, and the determining comprises comparing an appearance information for the antimicrobial that is administered to treat a microbe a human has to an appearance information for the antimicrobial that is not administered to the human, and determining the minimum inhibitory concentration based on the comparing.

* * * * *